United States Patent
Kumakura

(10) Patent No.: US 6,861,655 B2
(45) Date of Patent: Mar. 1, 2005

(54) NON-DESTRUCTIVE METHOD FOR TESTING CURING LEVEL OF CURED PRODUCT OF CURABLE ADHESIVE COMPOSITION AND MANUFACTURING METHOD OF ELECTRONIC DEVICES

(75) Inventor: Hiroyuki Kumakura, Kanuma (JP)

(73) Assignee: Sony Chemicals Corp., Tokyo (JP)

( * ) Notice: Subject to any disclaimer, the term of this patent is extended or adjusted under 35 U.S.C. 154(b) by 135 days.

(21) Appl. No.: 10/340,781

(22) Filed: Jan. 13, 2003

(65) Prior Publication Data

US 2003/0164457 A1 Sep. 4, 2003

(30) Foreign Application Priority Data

Feb. 25, 2002 (JP) ........................................ 2002-047912

(51) Int. Cl.[7] .............................................. G01N 21/64
(52) U.S. Cl. ..................................... 250/459.1; 438/14
(58) Field of Search ....................... 250/459.1; 438/14; 428/343, 346, 418, 620; 430/18; 522/31, 66

(56) References Cited

U.S. PATENT DOCUMENTS

| | | | | |
|---|---|---|---|---|
| 4,642,321 A | * | 2/1987 | Schoenberg et al. | 523/400 |
| 4,774,188 A | * | 9/1988 | Chandross | 436/5 |
| 4,859,807 A | * | 8/1989 | Swiggett et al. | 174/259 |
| 4,965,208 A | * | 10/1990 | Blitchington et al. | 436/5 |
| 5,426,008 A | * | 6/1995 | Hagiwara et al. | 430/18 |
| 6,265,460 B1 | * | 7/2001 | Kawate et al. | 522/31 |
| 6,706,417 B2 | * | 3/2004 | Konarski et al. | 428/620 |
| 2001/0028953 A1 | * | 10/2001 | Bluem et al. | 428/355 AC |
| 2003/0022403 A1 | * | 1/2003 | Shimoda et al. | 438/14 |

* cited by examiner

*Primary Examiner*—Otilia Gabor
(74) *Attorney, Agent, or Firm*—Oliff & Berridge, PLC

(57) ABSTRACT

In a method for non-destructively testing the curing level of the cured product of a curable adhesive composition, a fluorescent component that emits fluorescent light upon irradiation with excitation light is added to the curable adhesive composition, the curable adhesive composition containing this fluorescent component is cured, the cured product thus obtained is irradiated with excitation light, and the fluorescent light thus produced is observed to test the curing level of the cured product.

4 Claims, 3 Drawing Sheets

5 seconds at 170 ℃ (Example 1)

Before curing 5 seconds at 170 °C (Example 1)

5 seconds at 180 °C (Example 2)

5 seconds at 190 °C (Example 3)

5 seconds at 200 °C (Example 4)

5 seconds at 230 °C (Example 7)

NON-DESTRUCTIVE METHOD FOR TESTING CURING LEVEL OF CURED PRODUCT OF CURABLE ADHESIVE COMPOSITION AND MANUFACTURING METHOD OF ELECTRONIC DEVICES

BACKGROUND OF THE INVENTION

1. Field of the Invention

The present invention relates to a non-destructive method for testing the curing level of the cured product of a curable adhesive composition, and to a method for manufacturing an electronic device.

2. Description of the Related Art

In the manufacture of a semiconductor device or other such electronic device in which a bare chip IC or other such electronic parts are mounted on a wiring board, a resin press-bonding connection method featuring the use of a thermosetting paste-form or film-form anisotropic conductive adhesive or insulating adhesive, has been widely utilized because it reduces the number of manufacturing steps and improves productivity.

In this press-bonding connection method, one of the above-mentioned adhesive agents is supplied to the connection site between a wiring board and an electronic part, and heat and pressure are applied to cure the thermosetting adhesive, which ensures good connection reliability. Connection reliability, however, depends on the reactivity of the thermosetting adhesive, and the higher is the reactivity, the higher is the level of curing, and the better is the connection reliability. Ensuring satisfactory connection reliability therefore generally requires that the curing level be raised by increasing the reactivity to between 60 and 90%.

Accordingly, measuring the reactivity of a cured product of thermosetting adhesive after connection (that is, after curing) is essential to ensuring the connection reliability of electronic elements. Such measurement has been performed in the past by FT-IR and DSC methods.

Nevertheless, when an FT-IR or DSC method was used to measure the reactivity of a cured thermosetting adhesive present at the connection site between a wiring board and an electronic part in an electronic device in which said electronic part was mounted to the wiring board, a problem that was encountered was that the electronic device had to be destroyed to collect the cured thermosetting adhesive for testing. Also, this measurement generally took at least several hours, so testing efficiency was poor. This same problem also occurred in measuring the reactivity of the cured product of an active energy-curing type of adhesive that cures when irradiated with UV rays or other such active energy rays.

SUMMARY OF THE INVENTION

It is an object of the present invention to solve the above problems encountered in the past, and to allow the curing level of a curable adhesive that has been cured (that is, the cured product) at the connection site between a wiring board and an electronic part in an electronic device in which said electronic part is mounted on the wiring board, to be tested efficiently and in a non-destructive manner.

The inventor perfected the present invention upon discovering that the curing level of a cured product can be non-destructively and efficiently tested by adding a fluorescent component that emits fluorescent light when irradiated with excitation light to a curable adhesive composition, irradiating the cured product of the curable adhesive composition with light, and observing the fluorescent light thus produced.

Specifically, the present invention provides a method for the non-destructive testing of the curing level of the cured product of a curable adhesive composition, wherein a fluorescent component that emits fluorescent light upon irradiation with excitation light is added to the curable adhesive composition, the curable adhesive composition containing this fluorescent component is cured, the cured product thus obtained is irradiated with excitation light, and the fluorescent light thus produced is observed to test the curing level of the cured product.

The present invention also provides a method for manufacturing an electronic device consisting of a wiring board and electronic parts mounted thereon, comprising the steps of:

(a) tacking temporarily the electronic parts to the wiring board via a curable adhesive composition, where this curable adhesive composition contains a fluorescent component that emits fluorescent light upon irradiation with excitation light;

(b) then curing said curable adhesive composition; and (c) testing the curing level of the cured product by irradiating the cured product thus obtained with excitation light and observing the fluorescent light thus produced.

DESCRIPTION OF THE PREFERRED EMBODIMENTS

Figure 1:
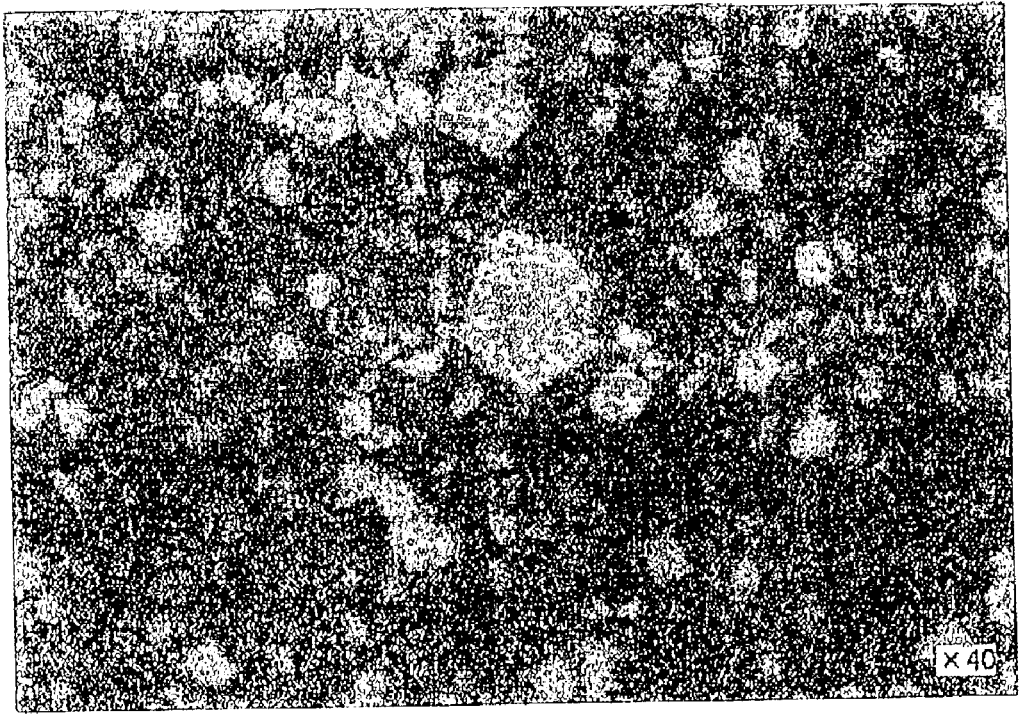
FIG. 1 is a photograph showing the results of observing fluorescent light from a thermosetting adhesive composition prior to curing.
Figure 2:
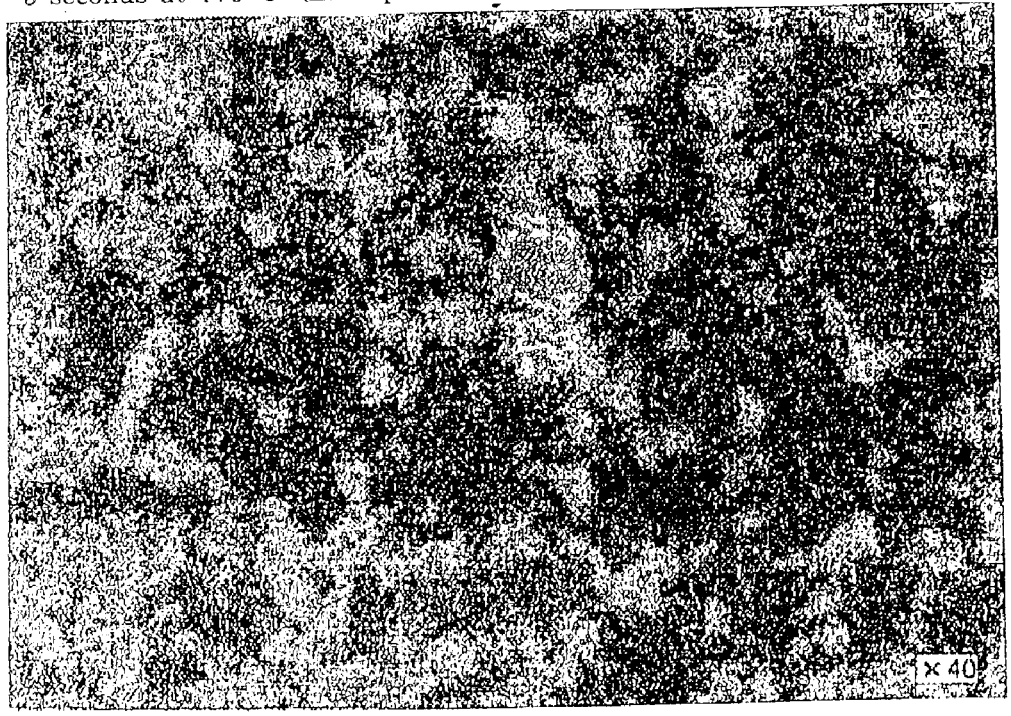
FIG. 2 is a photograph showing the results of observing fluorescent light from the cured product of the thermosetting adhesive composition in Example 1.
Figure 3:
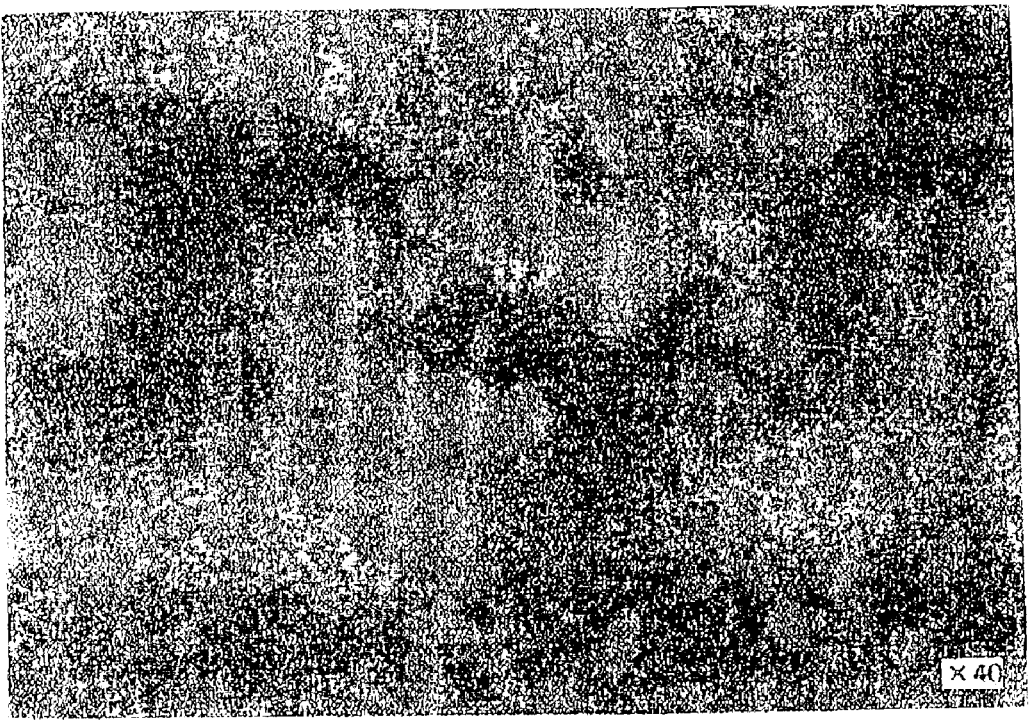
FIG. 3 is a photograph showing the results of observing fluorescent light from the cured product of the thermosetting adhesive composition in Example 2.
Figure 4:
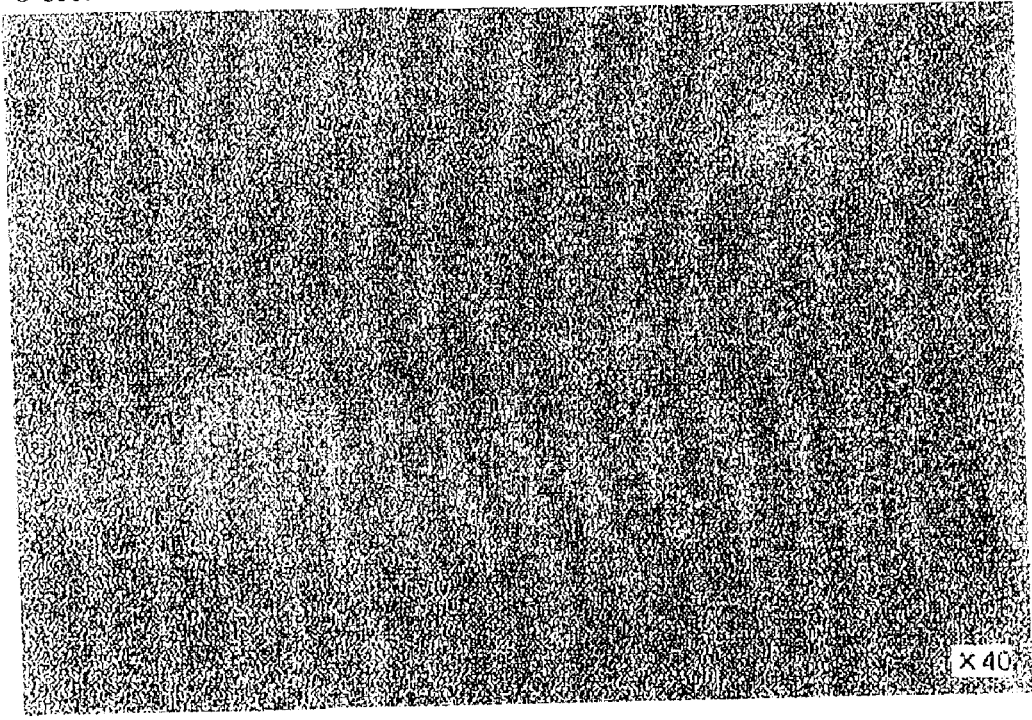
FIG. 4 is a photograph showing the results of observing fluorescent light from the cured product of the thermosetting adhesive composition in Example 3.
Figure 5:
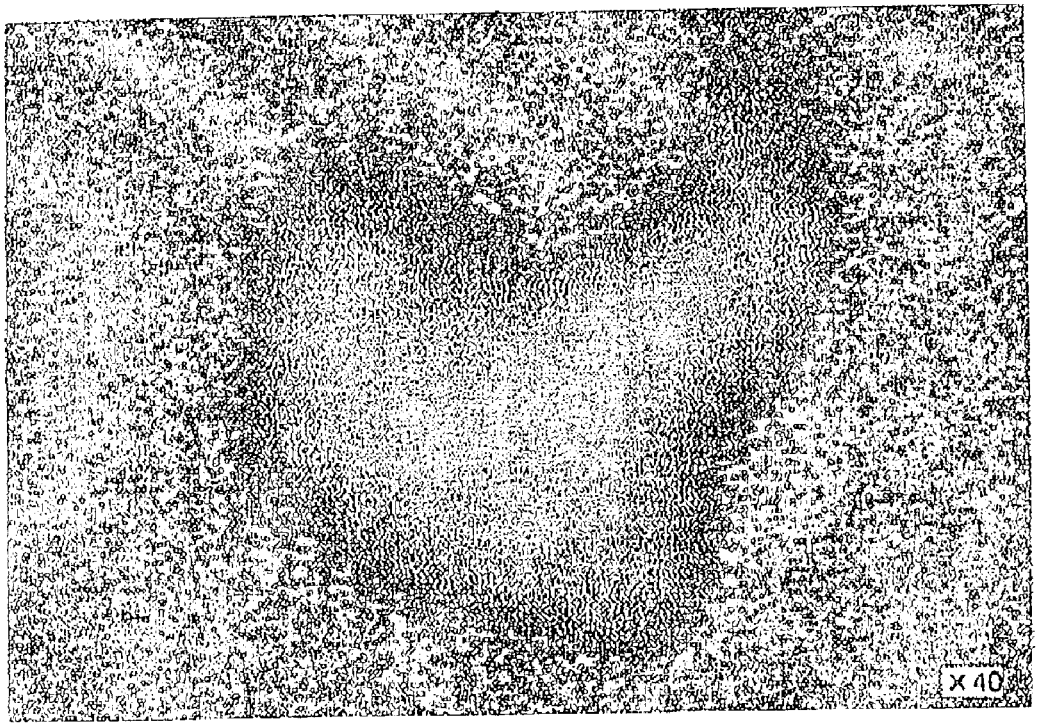
FIG. 5 is a photograph showing the results of observing fluorescent light from the cured product of the thermosetting adhesive composition in Example 4.
Figure 6:
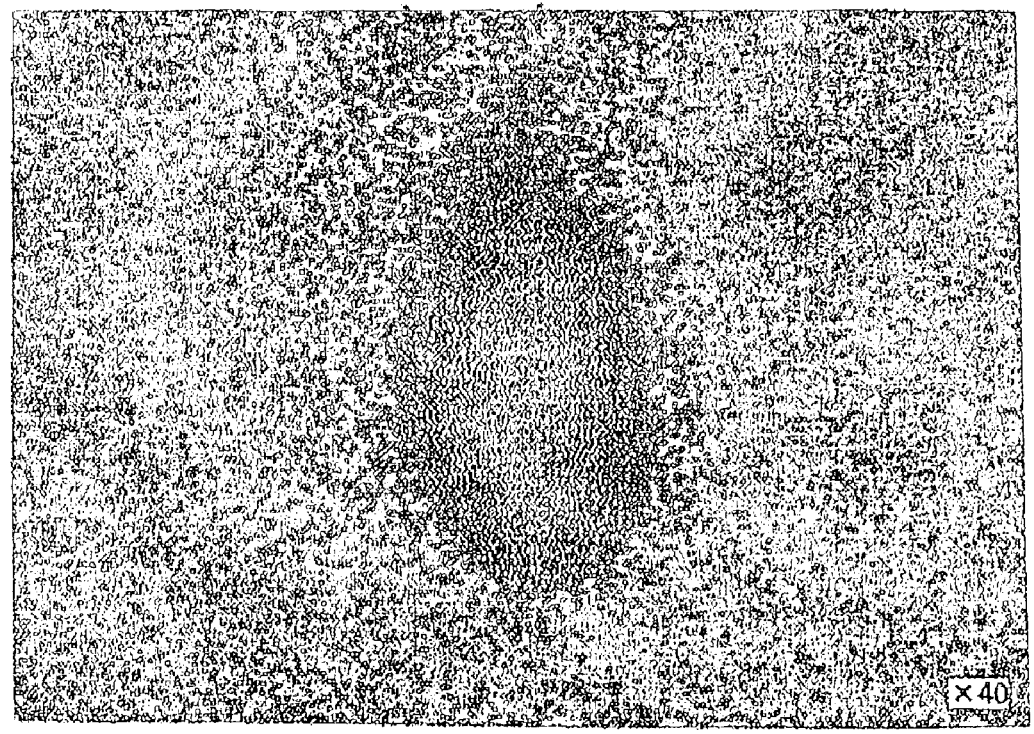
FIG. 6 is a photograph showing the results of observing fluorescent light from the cured product of the thermosetting adhesive composition in Example 7.

An example of the present invention will now be described in detail.

The present invention is a method for testing the curing level of the cured product of a curable adhesive composition by curing a curable adhesive composition containing a fluorescent light that emits fluorescent light when irradiated with excitation light, irradiating the cured product thus obtained with excitation light, and observing the fluorescent light thus produced. The fluorescent light emitted by the fluorescent component here can be observed through a glass substrate, and even when the curable adhesive composition is applied to an electronic device, the fluorescent light can still be observed through a glass substrate. This makes possible the non-destructive testing of the fluorescent light of a cured curable adhesive composition (that is, its cured product).

In the present invention, the reason the curing level (or reactivity) can be tested by observing the fluorescent light is that a correlation can be found between the curing level (or reactivity) and a certain index that specifies the produced fluorescent light (such as light emission intensity or light emission distribution).

For instance, in regard to the index of light emission distribution, when a thermosetting adhesive is used as the curable adhesive composition, an example is the use of a component that is not miscible in the thermosetting adhesive composition prior to the thermosetting of the thermosetting adhesive composition, but that gradually becomes miscible in the composition when heated for curing, as the fluorescent component. In this case, since the component is not miscible in the composition, the state of fluorescent light emission prior to curing is one in which the silhouette of the fluorescent component particles can be clearly observed in the composition. As the composition cures through heating (as its reactivity increases), the fluorescent component dissolves into the composition, the silhouette of the particles gradually blurs, and the entire composition eventually emits light uniformly. An example of this combination of a fluorescent component and a thermosetting adhesive resin is to use a hot-melt latent curing agent (such as an imidazole-based latent curing agent) as the fluorescent component, and an epoxy resin as the thermosetting adhesive resin. It is preferable here to visually or numerically determine the correlation between the curing level (or reactivity) and the light emission distribution in the planar direction in advance.

As to the index of light emission intensity, an example is the use of a component that reacts with the curable adhesive resin as thermosetting or active energy curing proceeds (as the reactivity increases), resulting in a decrease in light emission intensity. The curing adhesive resin may itself be a fluorescent substance, in which case the curing adhesive resin should be one whose own light emission intensity decreases as curing proceeds, or one whose light emission intensity decreases upon reaction with another component.

In the present invention a known fluorescent measurement apparatus can be used to observe the fluorescent light, and it is preferable to use a known incident-light fluorescent microscope or the like for observation.

The excitation light used to release the fluorescent light from the fluorescent component will vary with the type of fluorescent component, but when an imidazole-based latent curing agent is used, examples include light with a wavelength of 330 to 580 nm, and light obtained from a mercury vapor lamp light source.

The curable adhesive composition may be in the form of a paste, liquid, or film, just as with a conventional adhesive composition.

In addition to the thermosetting adhesive resin or active energy curing adhesive resin and the fluorescent component, the curable adhesive composition can also contain anisotropic conductive connection-use conductive particles, a plasticizer, a filler, or the like.

The testing method of the present invention can be applied favorably to the manufacture of an electronic device consisting of a wiring board and an electronic part mounted thereon.

Specifically, this method for manufacturing an electronic device consisting of a wiring board and an electronic part mounted thereon comprises the following steps (a) to (c).

Step (a)

First, an electronic part (such as a semiconductor element) is temporarily tacked to a wiring board (such as a flexible wiring board used for mounting semiconductor elements) via a curable adhesive composition containing a fluorescent component that emits fluorescent light when irradiated with excitation light. This temporary tacking can be accomplished by making use of the pressure-sensitive adhesiveness of the curable adhesive composition, and applying relatively moderate pressure.

Step (b)

Next, the curable adhesive composition is thermoset. The curing device to be used and the main curing conditions to be employed can be determined as dictated by the type of curing adhesive resin being used, the type of fluorescent component, and so on.

Step (c)

The cured product thus obtained is irradiated with excitation light, and the fluorescent light thus produced is observed with a known fluorescent measurement device (such as an incident-light fluorescent microscope), allowing the curing level (or reactivity) of the cured product of the curable adhesive composition to be non-destructively tested. The curing level here can be evaluated by measuring ahead of time the reactivity of the cured products of curable adhesive compositions of different curing levels by FT-IR or DSC method, two-dimensionally plotting on a graph the correlation of the resulting reactivity to the produced fluorescent light, and applying to this correlation the fluorescent light data observed for the cured product whose curing level is to be evaluated.

If the testing in step (c) reveals that the curing level of the cured product of the curable adhesive composition has not reached the desired level, the obtained electronic device may be discarded as defective, or it may again be subjected to step (b) and, if needed, to step (c). This allows the manufacturing yield to be raised. If the curing level is satisfactory, sealing or other such steps can be carried out as needed and the provide shipped out as a finished product.

EXAMPLES

The present invention will now be described in specific terms through examples.

Examples 1 to 7

The thermosetting adhesive compositions shown in Table 1 were molded by casting into anisotropic conduction adhesive films with a thickness of 25 $\mu$m.

TABLE 1

| Component | Wt parts |
| --- | --- |
| Phenoxy resin (YP50, Toho Chemical) | 30 |
| Naphthalene-type epoxy resin (HP4032D, Dainippon Ink & Chemicals) | 30 |
| Imidazole-based latent curing agent (HX3941HP, Asahi Chemical Epoxy) | 40 |
| Ni-Au covered acrylic particles (5 $\mu$m diameter) | 20 |

The anisotropic conduction adhesive films thus obtained were sandwiched between an ITO electrode (10 ohms/square) of a glass substrate with a thickness of 0.7 mm and an IC chip measuring 20 mm square and 2 mm thick and equipped with gold bumps (25 $\mu$m long, 90 $\mu$m wide, 20 $\mu$m high, pitch=80 $\mu$m). A constant heating type of heating head whose heating surface was coated with Teflon (registered trademark) in a thickness of 50 $\mu$m was used to produce a semiconductor device by hot-pressing for 5 seconds under the connection temperature conditions in Table 2 at a thrust of 40 Mpa.

The semiconductor devices thus obtained were subjected to a connection reliability test, a reactivity test, and fluorescent light observation, which are described below. The results obtained in these tests are given in Table 2.

Connection Reliability Test

The semiconductor device was aged for 1000 hours in an oven that had been adjusted to a temperature of 85° C. and a relative humidity of 85%. The device passed the test if the increase in electrical resistance between the connection terminals after aging was less than 5 Ω, which is indicated in Table 2 by "G," and failed if the resistance was 5 Ω or higher, indicated by "NG" in Table 2.

Reactivity Test

The cured product of the thermosetting adhesive composition was sampled from directly under the middle of the IC chip of the semiconductor device, and an FT-IR chart was prepared for this cured product sample (FT-IR device used was a UMA-500 made by Bio-Rad). The ratio between the absorbancy of epoxy groups in this chart (near 914 $cm^{-1}$) and the absorbancy of methyl groups (near 2920 $cm^{-1}$) was compared with that of the thermosetting adhesive composition prior to curing, and the reactivity was calculated. The results thus obtained are given in Table 2.

Fluorescent Light Observation

The cured product of the thermosetting adhesive composition was non-destructively observed from the glass substrate side of the resulting semiconductor device using an incident-light fluorescent microscope (BX51, made by Olympus Optical; objective lens: Uplan FI (40 power); light source: 100 W mercury vapor apo lamphouse U-LH100HGAPO; excitation method: wide band IB excitation U-MWIB2; excitation filter: BP460-490; dichroic mirror: DM505; absorption filter: BA510IF). If the silhouettes of particles of the latent curing agent that emit fluorescent light were observed, the curing level was deemed unsatisfactory (insufficient reactivity), indicated by "NG" in Table 2, but if the silhouettes of particles of the latent curing agent that emit fluorescent light were not observed, the curing level was deemed acceptable (sufficient reactivity), indicated by "G" in Table 2. FIGS. 2 to 6 are photographs showing the results of observing fluorescent light from the cured products of the thermosetting adhesive compositions in the obtained semiconductor devices. FIG. 1 is a photograph showing the results of observing fluorescent light from a thermosetting adhesive composition prior to curing.

TABLE 2

| Example | Connection temp. (° C.) | Connection reliability | FT-IR reactivity (%) | Fluorescent light observation results | Photograph |
|---|---|---|---|---|---|
| 1 | 170 | NG | 35 | NG | FIG. 2 |
| 2 | 180 | NG | 51 | NG | FIG. 3 |
| 3 | 190 | G | 66 | G | FIG. 4 |
| 4 | 200 | G | 73 | G | FIG. 5 |
| 5 | 210 | G | 77 | G | — |
| 6 | 220 | G | 81 | G | — |
| 7 | 230 | G | 83 | G | FIG. 6 |

It can be seen from Table 2 and FIGS. 1 to 6 that when the silhouettes of particles of an imidazole-based latent curing agent can be observed by fluorescent light observation, the reactivity is low (less than 60%), but when the silhouettes cannot be clearly discerned, the reactivity rises to 60% or more. This is because an imidazole-based latent curing agent emits fluorescent light when irradiated with ultraviolet rays, but the other components (epoxy resin, etc.) do not emit fluorescent light, so in a state of low reactivity, even if the particles of latent curing agent do melt, they will not be sufficiently miscible in the surrounding adhesive composition, so their silhouettes can be clearly discerned, whereas in a state of high reactivity, the particles of latent curing agent thoroughly melt in the adhesive composition and their silhouettes can no longer be discerned. Therefore, in the case of these examples, whether or not the curing level of the cured product of the thermosetting adhesive compositions had reached the level at which good connection reliability is obtained could be simply and efficiently determined by non-destructive testing through fluorescent light observation of the cured product of the thermosetting adhesive.

With the present invention, the reactivity of a curable adhesive that has been cured (that is, the cured product) at the connection site between a wiring board and an electronic part in an electronic device in which said electronic part is mounted on the wiring board can be testing efficiently and non-destructively.

The entire disclosure of the specification, claims, summary and drawings of Japanese Patent Application No. 2002-47912 filed on Feb. 25, 2002 is hereby incorporated by reference.

What is claimed is:

1. A non-destructive method for testing the curing level of the cured product of a curable adhesive composition, wherein a fluorescent component that emits fluorescent light upon irradiation with excitation light is added to said curable adhesive composition, the curable adhesive composition containing this fluorescent component is cured and the fluorescent component gradually becomes miscible in the curable adhesive composition when cured, the cured product thus obtained is irradiated with excitation light, and the fluorescent light thus produced is observed to test the curing level of said cured product by observing the extent to which a silhouette of particles of the fluorescent component has blurred.

2. The testing method according to claim 1, wherein said curable adhesive composition exhibits a thermosetting property, and said fluorescent component is a hot-melt latent curing agent.

3. The testing method according to claim 2, wherein said hot-melt latent curing agent is an imidazole-based latent curing agent.

4. A method for manufacturing an electronic device consisting of a wiring board and electronic parts mounted thereon, comprising the steps of:
    (a) tacking temporarily the electronic parts to the wiring board via a curable adhesive composition, where this curable adhesive composition contains a fluorescent component that emits fluorescent light upon irradiation with excitation light;
    (b) then curing said curable adhesive composition, the fluorescent component gradually becoming miscible in the curable adhesive composition when cured; and
    (c) testing the curing level of the cured product by irradiating the cured product thus obtained with excitation light and observing the extent to which a silhouette of particles of the fluorescent component has blurred in the fluorescent light thus produced.

* * * * *